US00PP34601P2

(12) United States Plant Patent
Glawe et al.

(10) Patent No.: US PP34,601 P2
(45) Date of Patent: Sep. 20, 2022

(54) ***PELARGONIUM* PLANT NAMED 'KLEPZ21614'**

(50) Latin Name: ***Pelargonium peltatum* (L.) L'Hér. ex Aiton x *Pelargonium zonale* (L.) L'Hér. ex Aiton**
Varietal Denomination: KLEPZ21614

(71) Applicant: KLEMM + SOHN GMBH & CO. KG, Stuttgart (DE)

(72) Inventors: Martin Glawe, Stuttgart (DE); Nina Neu, Weissach im Tal (DE)

(73) Assignee: KLEMM+SOHN GMBH & CO. KG, Stuttgart (DE)

( * ) Notice: Subject to any disclaimer, the term of this patent is extended or adjusted under 35 U.S.C. 154(b) by 0 days.

(21) Appl. No.: 17/736,400

(22) Filed: May 4, 2022

(30) Foreign Application Priority Data

Jun. 2, 2021 (CH) ..... 21-3440

(51) Int. Cl.
*A01H 5/02* (2018.01)
*A01H 6/42* (2018.01)

(52) U.S. Cl.
USPC ..... Plt./324
CPC ..... *A01H 6/425* (2018.05)

(58) Field of Classification Search
USPC ..... Plt./324
CPC ..... A01H 6/425; A01H 5/02
See application file for complete search history.

*Primary Examiner* — Keith O. Robinson
(74) *Attorney, Agent, or Firm* — Weatherly IP Solutions, LLC; James M. Weatherly

(57) ABSTRACT

A new *Pelargonium* plant particularly distinguished by single, light purple, pink flowers with a red eye and a dark green leaf color, is disclosed.

1 Drawing Sheet

Genus and species: *Pelargonium peltatum* (L.) L'Hér. ex Aiton x *Pelargonium zonale* (L.) L'Hér. ex Aiton.
Variety denomination: 'KLEPZ21614'.

CROSS-REFERENCE TO RELATED APPLICATION

This patent application claims the benefit of priority from Switzerland Plant Breeders Rights Application No. 21-3440 as filed on Jun. 2, 2021, the contents of which is incorporated herein by reference for all it teaches and discloses.

BACKGROUND OF THE NEW PLANT

The present invention comprises a new and distinct variety of *Pelargonium*, botanically known as *Pelargonium peltatum* (L.) L'Hér. ex Aiton x *Pelargonium zonale* (L.) L'Hér. ex Aiton and hereinafter referred to by the variety name 'KLEPZ21614'. 'KLEPZ21614' originated from a hand-pollination in July 2016 in Nairobi, Kenya between the female *Pelargonium* variety 'Rose Splash' (not patented) and the male *Pelargonium* variety 'Lilac Splash' (not patented).

Seeds from the hand-pollination were obtained. The seeds were sown and plants were grown for evaluation. A single plant was selected in June 2017 and subsequently named 'KLEPZ21614'. In July 2017 'KLEPZ21614' was first vegetatively propagated by vegetative stem cuttings in Stuttgart, Germany. 'KLEPZ21614' was found to reproduce true to type in successive generations of asexual propagation via vegetative cuttings in Stuttgart, Germany.

SUMMARY

The following are the most outstanding and distinguishing characteristics of this new variety when grown under normal horticultural practices in Stuttgart, Germany.

1. Single, light purple, pink flowers with a red eye; and
2. A dark green leaf color.

DESCRIPTION OF THE PHOTOGRAPH

This new *Pelargonium* plant is illustrated by the accompanying photograph which shows an overall view of the plant in a pot. The photograph is of an approximately 14-week-old plant grown indoors in Stuttgart, Germany, in March 2022. The colors shown are as true as can be reasonably obtained by conventional photographic procedures.

DESCRIPTION OF THE NEW VARIETY

The following detailed descriptions set forth the distinctive characteristics of 'KLEPZ21614'. The data which define these characteristics were collected from asexual reproductions carried out in Stuttgart, Germany. Data was collected on 3-month-old plants in Stuttgart, Germany under greenhouse conditions in March 2022. Color references are to The R.H.S. Colour Chart of The Royal Horticultural Society of London (R.H.S.), 6$^{th}$ edition (2015).

Classification:
*Family.*—Geraniaceae.
*Botanical.*—*Pelargonium peltatum* (L.) L'Hér. ex Aiton x *Pelargonium zonale* (L.) L'Hér. ex Aiton.
*Common.*—*Pelargonium.*
*Designation.*—'KLEPZ21614'.

Parentage:
*Female parent.*—'Rose Splash' (not patented).
*Male parent.*—'Lilac Splash' (not patented).

Plant:
*Form.*—Bushy.
*Habit.*—Mounding.
*Height* (*from top of soil*).—15.0 cm.

*Width* (*horizontal plant diameter*).—21.0 cm.
*Natural flowering season.*—March to October.
*Propagation type.*—Vegetative by stem cuttings.
*Time to produce a finished flowering plant.*—12 weeks.
*Time to initiate and develop roots.*—4 weeks.
*Root description.*—Fine, dense, RHS N155A (White).

Stems:
*Quantity of stems per plant.*—3.
*Color.*—RHS 138A.
*Surface texture.*—Pubescent, sparse.
*Stem form.*—Round.
*Diameter.*—0.8 cm.
*Length.*—8.0 cm.
*Internode length.*—1.0 cm.
*Anthocyanin.*—Present.

Leaves:
*Arrangement.*—Alternate.
*Shape.*—Reniform.
*Apex.*—Round.
*Base.*—Open.
*Margin.*—Crenate.
*Surface texture.*—Upper surface: Sparsely pubescent. Lower surface: Sparsely pubescent.
*Length.*—7.4 cm.
*Width.*—8.5 cm.
*Color.*—Upper surface: RHS N137A. Lower surface: RHS 137B.
*Petiole.*—Length: 4.2 cm. Diameter: 0.4 cm. Color: RHS 137B. Strength: Medium.
*Venation pattern.*—Palmate.
*Venation color.*—Upper surface: RHS 138A. Lower surface: RHS 143C.
*Zonation.*—Absent.

Inflorescence:
*Lastingness of flowers on the plant.*—6 to 8 days.
*Flower type.*—Single.
*Umbels.*—Quantity of umbels per plant: 5 to 7. Length: 5.5 cm. Diameter: 9.0 cm.
*Individual florets of the umbel.*—Quantity of florets per umbel: 10 to 13. Depth: 1.0 cm. Diameter: 5.0.
*Fragrance.*—Absent.

Flower buds:
*Cluster shape.*—Round.
*Cluster size.*—Length: 1.2 cm. Width: 1.5 cm.
*Surface texture.*—Moderately pubescent.
*Bud.*—Height: 1.2 cm. Width: 0.5 cm. Shape: Round. Apex: Acute. Base: Obtuse. Margin: Entire. Color: RHS 138A.

Petals:
*Quantity per flower.*—5.
*Shape.*—Spatulate.
*Apex.*—Round.
*Base.*—Obtuse.
*Margin.*—Entire.
*Length.*—2.4 cm.
*Width.*—2.5 cm.
*Surface texture.*—Upper surface: Smooth. Lower surface: Smooth.
*Color of lobes.*—Upper lobes: Upper surface: RHS 65A (margin and center), RHS 46B (spot). Lower surface: RHS 69B. Lower lobes: Upper surface: RHS 65A (margin and center), RHS 46B (spot). Lower surface: RHS 69B.

Petaloids: Absent.

Sepals:
*Number per flower.*—5.
*Shape.*—Elliptic.
*Apex.*—Acute.
*Base.*—Obtuse.
*Margin.*—Entire.
*Surface texture.*—Upper surface: Smooth. Lower surface: Moderately pubescent.
*Color.*—Upper surface: RHS 144A. Lower surface: RHS 146A.
*Length.*—1.4 cm.
*Width.*—0.4 cm.

Pedicel:
*Length.*—3.0 cm.
*Diameter.*—0.1 cm.
*Color.*—RHS 177B.
*Surface texture.*—Sparsely pubescent.
*Strength.*—Medium.

Peduncle:
*Length.*—7.2 cm.
*Diameter.*—0.4 cm.
*Color.*—RHS 148A.
*Texture.*—Moderately pubescent.
*Strength.*—Medium.

Reproductive organs:
*Stamens.*—Quantity per flower: 5. Anther length: 0.2 cm. Filament length: 0.6 cm. Filament color: RHS 69C. Pollen amount: Moderate. Pollen color: RHS 173B.
*Pistils.*—Number: 1. Stigma color: RHS 67A. Style length: 0.5 cm. Style color: RHS 67A. Ovary arrangement: Central. Ovary color: RHS 143A. Ovary diameter: 0.2 cm. Ovary length: 0.5 cm.

Fruit and seed set: None observed.

Disease and pest/insect resistance: None observed.

COMPARISON WITH PARENTAL LINES AND KNOWN VARIETY

'KLEPZ21614' is distinguished from its parents as described in Table 1.

TABLE 1

Comparison with Parental Lines

| Characteristic | 'KLEPZ21614' | Female parent 'Rose Splash' | Male parent 'Lilac Splash' |
|---|---|---|---|
| Flower color | Light purple-pink, with red eye | Magenta with red eye and white center | Purple-pink with red eye |

'KLEPZ21614' can be compared to the commercial variety 'Lieke Pink Eye' (not patented). Differences between the two varieties are described in Table 2.

TABLE 2

Comparison with Similar Variety

| Characteristic | 'KLEPZ21614' | 'Lieke Pink Eye' |
|---|---|---|
| Flower type | Single | Semi-double |
| Leaf color | Dark green | Green |

We claim:

1. A new and distinct variety of *Pelargonium* plant named 'KLEPZ21614' as illustrated and described herein.

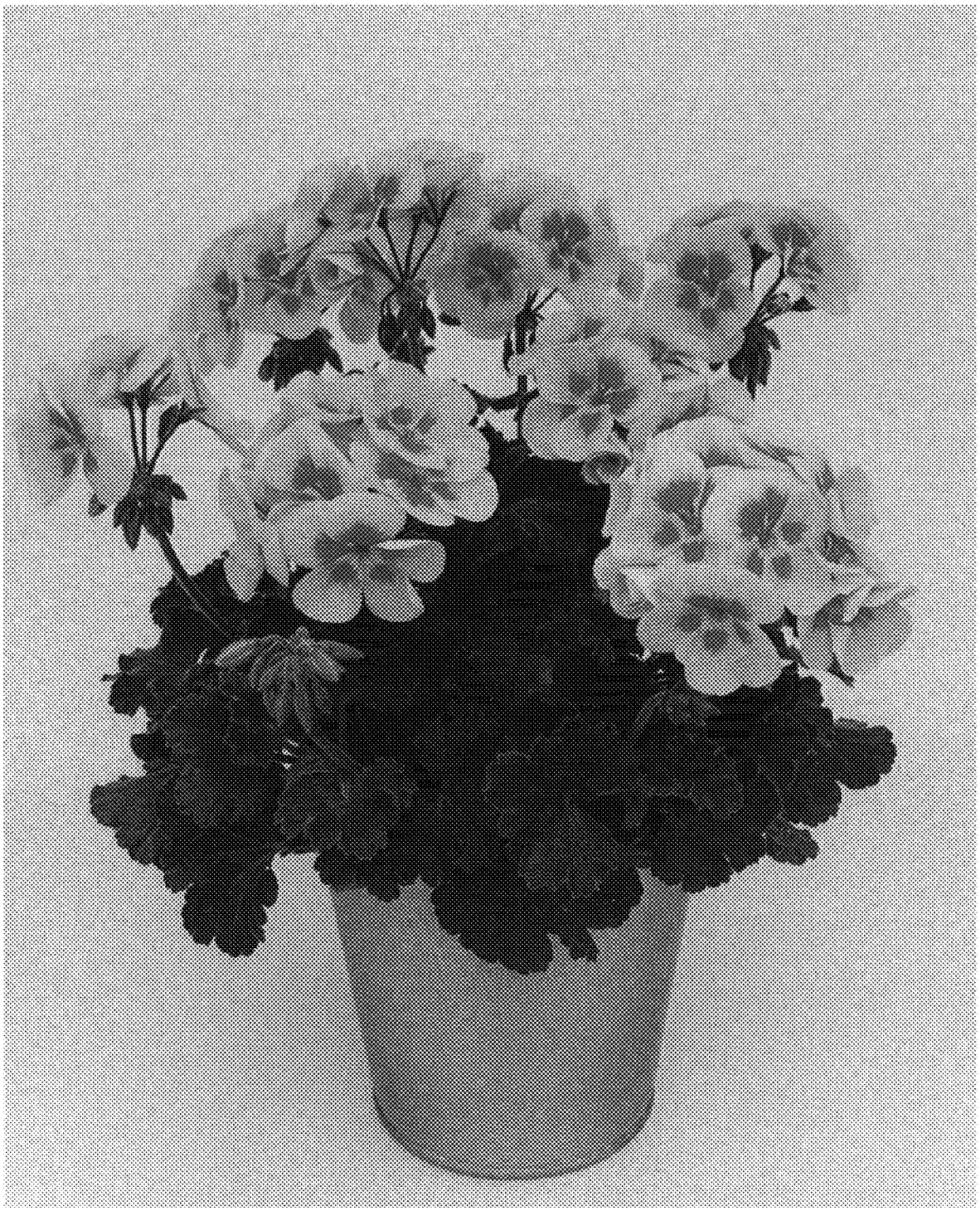

* * * * *